United States Patent [19]

Vanderlaan et al.

[11] Patent Number: 5,472,703
[45] Date of Patent: Dec. 5, 1995

[54] OPHTHALMIC LENS WITH ANTI-TOXIN AGENT

[75] Inventors: Douglas G. Vanderlaan, Jacksonville, Fla.; Susan K. Brown-Skrobot, Hamilton Square, N.J.; Clyde L. Schultz, Ponte Vedra Beach, Fla.

[73] Assignee: Johnson & Johnson Vision Products, Inc., Jacksonville, Fla.

[21] Appl. No.: 25,018

[22] Filed: Mar. 2, 1993

[51] Int. Cl.$^6$ .......................................... A61F 2/14
[52] U.S. Cl. .................. 424/429; 424/427; 623/4
[58] Field of Search .................... 424/427, 429; 623/4, 5

[56] References Cited

U.S. PATENT DOCUMENTS

| | | | |
|---|---|---|---|
| 4,485,029 | 11/1984 | Kato et al. | 252/106 |
| 4,921,279 | 6/1990 | Bawa et al. | 424/427 |

FOREIGN PATENT DOCUMENTS 0219207  4/1987  European Pat. Off. .
0395099  10/1990 European Pat. Off. .

OTHER PUBLICATIONS

Meslard et al. (Polym. Prepr. Am. Chem. Soc., Div. Polym. Chem. 30 pp. 488–489 (1989).

Schwartz et al. (Am. J. Ophthalmol., 109, pp. 701–704).

*Primary Examiner*—Carlos Azpuru

[57] ABSTRACT

An ophthalmic lens for placement on the anterior surface of the eye is disclosed. The lens has impregnated in it or it has coated on its surface an ester of a polyhydric aliphatic alcohol and a fatty acid in which the alcohol residue has at least one hydroxyl group. The ester is present in an amount which is effective to prevent or decrease the release of bacterial toxins when the lens is exposed to those toxins. The lens is particularly well-suited for a soft hydrogel contact lens, and advantageously eliminates, minimizes or prevents keratitis. Bacterial keratitis is an infection of the cornea of the eye which may occur during extended wear of the lens and may cause ulceration of the cornea.

14 Claims, No Drawings

OPHTHALMIC LENS WITH ANTI-TOXIN AGENT

BACKGROUND OF THE INVENTION

This invention relates to an ophthalmic lens with improved properties especially adapted for extended wear applications. More specifically, it relates to an ophthalmic lens which contains a compound capable of preventing or decreasing the release of bacterial toxins into the eye.

A dramatic shift has taken place over the past decade concerning ophthalmic lens technology, and improvements in this technology have led to changes in the manner in which ophthalmic lenses can be worn by the patient. As technology has advanced, it is now possible to wear ophthalmic lenses for extended periods of time, even during periods of sleep. This has occurred because these lenses, particularly contact lenses, have become more compatible with delicate eye tissue. Consequently, patient comfort has increased to the point where the lens can be worn by the patient for extended periods without significant discomfort. The type of contact lens which is most closely associated with extended wear applications is a soft hydrogel lens, which consists of a hydrophilic polymer swollen with a substantial amount of water.

Unfortunately, the use of ophthalmic lenses for extended wear applications has not been free of problems. For example, bacterial infections of the cornea have been reported. In the presence of minor trauma to the outer surface of the cornea (epithelium), bacteria may enter and ultimately ulcerate the cornea (ulcerative keratitis), a condition which, if not properly treated, can be responsible for sight-threatening damage to the cornea.

While attempts have been made to make contact lenses which are capable of fighting off bacterial infections in general, little has been accomplished to design a lens which is capable of preventing or decreasing the release of toxins which may cause ulcerative keratitis. The common approach has been to impregnate the lens with a broad spectrum antimicrobial. Meslard et al. (Polym. Prepr. Am. Chem. Soc., Div. Polym. Chem. 30 p. 488–489 (1989)), describe a reversible chemical immobilization of indomethacin, which is an anti-inflammatory agent, onto ophthalmic hydrogels. The drug is hydrolytically cleaved and released from the lens on the eye. Schwartz et al. (Am. J. Ophthalmol., 109, pages 701–704) describe the use of contact lenses formed from collagen to release amphotericin B, which is an anti-fungal agent, to rabbit eyes. U.S. Pat. No. 4,931,279 describes a contact lens made with an ion exchange resin and a drug such as pilocarpine, which is an anti-glaucoma agent, for release into the eye. Finally, in a broad sense, European Patent Application 219,207 describes the use of hydrophobic polymers as drug delivery agents. It is possible to make ophthalmic lenses from such hydrophobic polymers.

The prior art attempts to minimize or eliminate diseases associated with extended wear of ophthalmic lenses all have a significant drawback. Although the use of broad spectrum antimicrobials may ward off undesirable bacteria, it is also likely to kill the normal biota of the tear fluid present in the eye. The elimination of "good" bacteria may in itself cause undesirable side effects resulting from the collapse of the eye's own immunodefense system. In addition, the large scale destruction of bacteria in the eye may lead to adverse reactions because of the release of toxins associated with the lysing of bacteria.

Another approach for preventing the deleterious effects of corneal infections is disclosed in U.S. Pat. No. 4,485,029. This patent describes an aqueous solution of glyceryl monolaurate for use as a cleaning, disinfecting and preserving system, for contact lenses. While immersing this lens in this solution may preserve the lens for a longer period than what otherwise would be possible, this technique would not prevent or decrease the release of bacterial toxins when exposed to such toxins on the eye of the wearer. This is so because the amount of glyceryl monolaurate inadvertently absorbed into or on the lens is insufficient to prevent or decrease the release of bacterial toxins.

In view of the deficiencies of the prior art, it would be desirable to develop an ophthalmic lens which is capable of preventing or decreasing the production of bacterial toxins when the lens is exposed to bacteria. In addition, it would be especially desirable if such a lens could be developed which has specific activity for eliminating the ulcerative toxins associated with bacterial keratitis.

SUMMARY OF THE INVENTION

The invention is an ophthalmic lens for placement on the anterior surface of the eye. The lens has impregnated in it, or it has coated on its surface, an ester of a polyhydric aliphatic alcohol and a fatty acid. The ester is present in an amount which is effective to prevent or decrease the release of bacterial toxins when the lens is exposed to those toxins. The ester can be selected from any of the following groups:

a) monoesters of a polyhydric aliphatic alcohol and a fatty acid containing from eight to eighteen carbon atoms and wherein said monester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of said monoesters and diesters.

Surprisingly, the incorporation of the ester into the ophthalmic lens significantly decreases or prevents the release of bacterial toxins when the lens is exposed to those toxins on the eye of the wearer. In addition, the fatty acid ester is advantageously selective in preventing or decreasing the release of bacterial toxins which may be associated with ulcerative keratitis. In this manner, ophthalmic lenses of this invention are capable of preventing the deleterious effects of these toxins without substantially affecting the normal flora of the tear fluid and without the other possible side-effects from broad spectrum antibiotics.

The ophthalmic lenses of this invention can be used for any application in which an ophthalmic lens is worn by a patient, but it is especially adapted for extended wear applications, even when the lens remains in place on the eye during sleep.

DETAILED DESCRIPTION OF THE INVENTION

For the purpose of defining this invention, an ophthalmic lens can be any lens which is designed for placement on the anterior surface of the eye. The preferred ophthalmic lens is a contact lens or a corneal bandage lens. The most preferred lens is a contact lens, particularly a soft hydrogel contact lens. The soft hydrogel lens is the lens most commonly worn for extended wear applications.

The preferred hydrogel contact lens is a synthetic polymeric lens. Preferably, the polymer from which the lens is derived is formed from polymerizing a monomer from the class of hydroxy esters of acrylic acid or methacrylic acid. The preferred monomer is hydroxyethylmethacrylate (HEMA). Advantageously, a crosslinking agent is added to the monomer composition from which the polymeric lens is derived to enhance the mechanical strength of the lens and consequently its handling properties. Crosslinking agents which can be used are polyfunctional monomers, such as ethylene glycol dimethacrylate (EGDMA).

The lens can be lathe cut from a polymeric lens blank, or it can be polymerized in a mold shaped in the form of a lens, with or without the presence of an inert diluent. In either case, the hydrogel lens is desirably swollen in water so that the composition of the lens is at least 30 weight percent water.

The ester for impregnating the ophthalmic lens or coating its surface is a monoester or diester in which there is at least one unreacted hydroxyl group when the polyhydric aliphatic alcohol is reacted with the fatty acid.

The fatty acid preferably has from eight to eighteen carbon atoms. The fatty acid portion of the aforementioned monoesters and diesters may be derived from caprylic, capric, lauric, myristic, palmitic and stearic acids, which are saturated fatty acids whose chain lengths, respectively, are $C_8$, $C_{10}$, $C_{12}$, $C_{14}$, $C_{16}$, and $C_{18}$. The fatty acid portion of the aforementioned monoesters and diesters may be derived as well from unsaturated fatty acids having carbon chain lengths also ranging from $C_8$ to $C_{18}$, one example of such unsaturated fatty acids being oleic acid. The preferred fatty acid for use in the practice of the present invention is lauric acid, a saturated fatty acid whose chemical formula is $C_{11}H_{23}COOH$.

As used in this specification and the appended claims, the term "aliphatic" has the meaning usually accorded it in organic chemistry, i.e. "aliphatic" refers to organic compounds characterized by straight—or branched—chain arrangement of the constituent carbon atoms.

As used in this specification and the appended claims, the term "polyhydric" refers to the presence in a chemical compound of at least two hydroxyl (OH) groups. Thus, a polyhydric aliphatic alcohol is one which has at least two hydroxyl groups and in which the carbon backbone is either straight or branched.

Polyhydric alcohols suitable for forming monoesters and/or diesters for use in the practice of the present invention are 1,2-ethanediol; 1,2,3-propanetriol (glycerol); 1,3-propanediol; 1,4-butanediol; 1,2,4-butanetriol and the like. The preferred polyhydric aliphatic alcohol for forming monesters and diesters for use in the practice of the present invention is 1,2,3-propanetriol (commonly called glycerol) whose formula is $HOCH_2CH(OH)CH_2OH$.

The esters which are especially useful in the practice of the present invention have at least one hydroxyl group associated with their aliphatic alcohol residue. Thus, it will be understood that the monoester of 1,2-ethanediol and one of the aforementioned fatty acids may be used in the practice of the present invention because said ester, whose general formula is

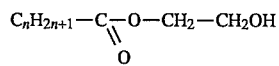

has at least one hydroxyl group (i.e. the hydroxyl group at the far right-hand side of the structural formula shown above) in that portion of the ester derived from the aliphatic alcohol 1,2-ethanediol. On the other hand, it will be understood that it would be undesirable to use the diester of 1,2-ethanediol and one of the aforementioned fatty acids in the practice of the present invention because the ester, whose general formula is

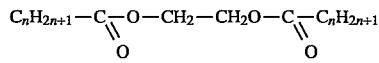

does not have at least one hydroxyl group in that portion of the ester derived from the 1,2-ethanediol. These diesters and other esters which do not have an hydroxyl group on their alcohol residue have not been found to possess a desired degree or antibacterial activity.

The monoester of glycerol and one of the designated fatty acids is desirably used in the practice of the present invention because that ester will have two hydroxyl groups associated therewith which are derived from the glycerol. The diester of glycerol and one of the designated fatty acids may also be used because that ester will have one hydroxyl group associated therewith which is derived from the aliphatic alcohol glycerol. Indeed, blends of glyceryl monolaurate and glycerol dilaurate may be useful in the practice of the present invention.

Preferred esters for use in the practice of the present invention are glyceryl monolaurate (GML), glyceryl dilaurate and mixtures thereof.

Particularly preferred is glyceryl monolaurate sold under the tradename "Monomuls 90 L-12" from Henkel Corporation. This compound contains about 96% by weight glyceryl monolaurate. Glyceryl monolaurate is a Generally Recognized As Safe (GRAS) listed compound by the FDA for use as a food emulsifier.

Other preferred esters for use in accordance with this invention include monolaurate derivatives of $C_3$ alkanols, such as 2-hydroxyl-1-propyl laurate and 3-hydroxy-1-propyl laurate. Dilaurate derivatives of $C_3$ alkanols such as glycerol-1,3-dilaurate, glycerol-1,2-dilaurate are also expected to reduce the amount of bacterial toxins produced. Ethylene glycol derivatives such as ethylene glycol monolaurate as well as polyethylene glycol laurates, e.g., diethylene glycol monolaurate and triethylene glycol monolaurate are also expected to be active. Certain polymers are also expected to have toxin-reducing activity, for example, polyethylene glycol (200 MW) monolaurate, polyethylene glycol (400 MW) monolaurate, polyethylene glycol (1000 MW) monolaurate, and polypropylene glycol laurates such as polypropylene glycol monolaurate.

Other fatty acid esters which are believed to be active against bacterial toxins for the ophthalmic lenses of this invention are: glyceryl monocaprylate, glyceryl caprate, a mixture of glyceryl monocaprylate and glyceryl caprate, glyceryl monomyristate, glyceryl monopalmitate, glyceryl monostearate and glyceryl monooleate.

The lens can be impregnated with the fatty acid ester using conventional methods. For example, the lens can be immersed in a solvent which swells the lens and dissolves the ester. The preferred solvents are volatile, short chain alcoholic solutions, e.g. ethanol. The solution is preferably a dilute aqueous solution with the concentration of the ester ranging from about 0.1 to about 10 weight percent, but preferably around 1 weight percent. The lens is left in the aqueous alcoholic solution for a time sufficient for the ester and the solvent to penetrate and swell the lens, and subsequently allow for the lens to equilibrate. Typically, this period of time can range between 2 to 3 hours. Afterwards, the lens is removed from solution, and the solvent is removed by simply allowing the lens to dry in air.

Alternatively, the lens can be impregnated by stirring the lens for at least several minutes in a suspension of molten ester in water or buffered saline.

It is also possible to coat the surface of the lens with the fatty acid ester. This may be particularly desirable when the lens is a hard lens or a soft hydrophobic lens. The coating of the outer surfaces of these lenses can be accomplished using conventional methods, such as by spraying, dipping or coating with a roller.

The amount of fatty acid ester which is effective to prevent or decrease production of bacterial toxins will depend on numerous factors, such as the specific toxin targeted and the extent of an existing infection, if any. This amount can be readily determined empirically. For most instances, and particularly when it is desired to prevent or decrease the production of bacterial toxins which may cause the ulceration and scarring associated with keratitis, the amount of ester impregnated in the lens or coated on its surface should range from about 0.05 to about 5.0 percent of the weight of the lens. If the amount of ester were less than about 0.05 weight percent, then the desired prevention or decrease of the bacterial toxins produced may not occur. If the amount of ester were greater than about 5.0 weight percent, then the fatty acid ester may interfere with the optical characteristics of the lens, or the ester may undesirably crystallize in the eye or in its package. Preferably, the amount of fatty acid ester is between about 0.5 to about 1.0 weight percent.

Numerous additional embodiments are within the scope of this invention, and may readily be realized by those skilled in this art. The following examples are intended merely to illustrate the preferred embodiments of this invention, and are not intended to represent all of the embodiments within the scope of the appended claims.

EXAMPLES

SAMPLE PREPARATION

105 Acuvue® contact lenses are placed into a solution of 1.0 gram of glyceryl monolaurate (GML) in 100 grams of reagent grade ethanol. After soaking for 16 hours the lenses are removed with a swab and placed on a silicone rubber sheet to air dry for 6 hours. Control lenses were immersed in reagent grade ethanol without GML and similarly dried. An additional set of control lenses were made by immersing ACUVUE lenses in isopropyl alcohol (IPA) and drying.

EXAMPLE 1

Sterile disposable centrifuge tubes containing 1.0 ml of sterile protein enriched Brain Heart Infusion Broth (BHI) had either a contact lens untreated or GML-treated or no lens at all (control). A 24 hour culture of TSST-1 producing *S. aureus* (FRI-1169) was grown in BHI broth with static conditions at 37° C. at which time an inocula of $10^8$ CFU were added to each vesicle. The tubes were incubated with static conditions at 37° C. After 24 hours the tubes were analyzed for both cell viability and toxin production. TSST-1 concentrations were determined by Enzyme Linked Immuno 25624 (ELISA) method reported by Resiser et. al. in Applied and Environmental Microbiology, December 1982, pp. 1349–1355 while viable cell counts were determined using conventional pour plate techniques.

The results of this experiment are presented in Table 1. The data show that GML contained within contact lenses was effective in reducing TSST-1 formation by 99%.

TABLE 1

EFFECT OF GML CONTACT LENSES ON EXOTOXIN PRODUCTION BY *S. AUREUS*

| DESCRIPTION | CONC. OF VIABLE S. Aureus CELLS ($Log_{10}$ CFU/ml) | CONC OF TSST-1 (ng/ml) | REDUCTION (%) |
|---|---|---|---|
| S. aureus 1169 (Inoculum only) | 9.80 | 1,750.93 | — |
| Control Lenses | 9.80 | 4,044.63 | — |
| IPA Lenses | 9.72 | 954.83 | — |
| GML Lenses | 8.71 | <10 | 99 |

EXAMPLE 2

Sterile disposable centrifuge tubes containing 1.0 ml of sterile BHI broth had either a contact lens (untreated or GML-treated) added to the medium or no lens at all (control) in quadruplicate. A 24 hour culture of exotoxin A producing *S. aureus* (FRI 100) was inoculated into BHI broth with static concentrations at 37° C. at which time $10^8$ CFU were added to each vesicle. The tubes were incubated with static conditions at 37° C. After 24 hours, the tubes were analyzed for both cell viability and exotoxin production. Enterotoxin A concentrations were determined using ELISA while cell viability was determined using the conventional pour plate technique.

The results in Table 2 show a 99% reduction in Enterotoxin A produced in the presence of GML-containing contact lenses.

TABLE 2

EFFECT OF GML CONTACT LENSES ON ENTEROTOXIN (ENT) A PRODUCTION

| SAMPLE | CONC. OF VIABLE S. AUREUS CELLS ($Log_{10}$ CFU/ml) | CONC. OF ENT A PRODUCED (ng/ml) | REDUCTION (%) |
|---|---|---|---|
| FRI-100 Inculum | 9.77 | 1,647 | — |
| Control Lenses (Control) | 9.83 | 1,160 | — |
| IPA Contact Lens | 9.84 | 1,488 | — |
| GML Contact Lens | 7.91 | 19 | 99 | n = 4

EXAMPLE 3

Sterile disposable centrifuge tubes containing 1.0 ml of sterile BHI broth had either a contact lens (untreated or GML-treated) added to all (control). A 24 hour culture of enterotoxin B producing S. aureus (MnHoch) was grown in BHI broth with static conditions at 37° C. at which time $10^8$ CFU were added to each vesicle. The tubes were incubated with static conditions at 37° C. After 24 hours, the tubes were analyzed for both cell viability and exotoxin production. Enterotoxin B concentrations were determined using ELISA while cell viability was determined using the conventional pour plate technique.

The results in Table 3 show a 99% reduction in Enterotoxin B produced in the presence of GML-containing contact lenses.

TABLE 3

| EFFECT OF GML CONTACT LENSES ON ENTEROTOXIN B PRODUCTION | | | |
|---|---|---|---|
| SAMPLE | CONC. OF VIABLE *S. AUREUS* CELLS ($Log_{10}$ CFU/ml) | CONC. OF ENT B PRODUCED (ng/ml) | REDUCTION (%) |
| Mn Hoch Inoculum | 10.15 | 19,317 | — |
| Contact Lens (Control) | 10.06 | 15,601 | — |
| IPA Contact Lens | 9.85 | 20,336 | — |
| GML Contact Lens | 7.80 | 18 | 99 | n = 4

EXAMPLE 4

Sterile disposable centrifuge tubes containing 1.0 ml of sterile BHI broth had either a contact lens (untreated or GML-treated) added to the medium or no lens at all (control) in quadruplicate. A 24 hour culture of enterotoxin C producing S. aureus (MnDon) was grown in BHI broth with static conditions at 37° C. After 24 hours, the tubes were analyzed for both cell viability and enterotoxin production. Enterotoxin C concentrations were determined using ELISA while cell viability was determined using the conventional pour plate technique.

The results in Table 4 show a 99% reduction in Enterotoxin C produced in the presence of a GML-containing contact lens.

TABLE 4

| EFFECT OF GML CONTACT LENSES ON ENTEROTOXIN C PRODUCTION | | | |
|---|---|---|---|
| SAMPLE | CONC. OF VIABLE *S. AUREUS* CELLS ($Log_{10}$ CFU/ml) | CONC. OF ENT C PRODUCED (ng/ml) | REDUCTION (%) |
| Mn Don Inoculum | 10.08 | 4,454 | — |
| Contact Lens (Control) | 10.05 | 6,421 | — |
| IPA Contact Lens | 10.07 | 7,630 | — |
| GML Contact Lens | 7.31 | 15 | 99 | n = 4

We claim:

1. A contact lens having impregnated therein, or coated on the surface thereof, an ester of a polyhydric aliphatic alcohol and a fatty acid, said ester of a polyhydric aliphatic alcohol and a fatty acid being present in an amount between about 0.05 and about 5.0 percent of the weight of the lens, and said ester being selected from the group consisting of:

a) monoesters of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of said monoesters and diesters.

2. The lens of claim 1 wherein the contact lens is a soft hydrogel contact lens.

3. The lens of claim 1 wherein said ester of a polyhydric aliphatic alcohol and a fatty acid is present in an amount between about 0.5 and about 1.0 weight percent.

4. The lens of claim 1 wherein said fatty acid is lauric acid.

5. The lens of claim 4 wherein said polyhydric alcohol is glycerol.

6. The lens of claim 5 wherein said ester of a polyhydric aliphatic alcohol and a fatty acid is glyceryl monolaurate.

7. The lens of claim 3 wherein said ester of a polyhydric aliphatic alcohol and a fatty acid comprises a mixture of glyceryl monolaurate and glyceryl dilaurate.

8. The lens of claim 3 wherein said ester of a polyhydric aliphatic alcohol and a fatty acid is glyceryl monocaprylate.

9. The lens of claim 3 wherein said ester of a polyhydric aliphatic alcohol and a fatty acid is glyceryl caprate.

10. The lens of claim 3 wherein said ester of a polyhydric aliphatic alcohol and a fatty acid comprises a mixture of glyceryl monocaprylate and glyceryl caprate.

11. The lens of claim 3 wherein said ester of a polyhydric aliphatic alcohol and a fatty acid is glyceryl monomyristate.

12. The lens of claim 3 wherein said ester of a polyhydric aliphatic alcohol and a fatty acid is glyceryl monopalmitate.

13. The lens of claim 3 wherein said ester of a polyhydric aliphatic alcohol and a fatty acid is glyceryl monostearate.

14. The lens of claim 3 wherein said ester of a polyhydric aliphatic alcohol and a fatty acid is glyceryl monooleate.

* * * * *